(12) United States Patent
Jugl et al.

(10) Patent No.: US 8,998,857 B2
(45) Date of Patent: Apr. 7, 2015

(54) CARTRIDGE HOLDER ASSEMBLY FOR A DRUG DELIVERY DEVICE

(75) Inventors: Michael Jugl, Frankfurt am Main (DE); Torsten Kraft, Frankfurt am Main (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 13/992,329

(22) PCT Filed: Dec. 20, 2011

(86) PCT No.: PCT/EP2011/073379
§ 371 (c)(1),
(2), (4) Date: Jun. 7, 2013

(87) PCT Pub. No.: WO2012/084927
PCT Pub. Date: Jun. 28, 2012

(65) Prior Publication Data
US 2013/0261560 A1 Oct. 3, 2013

(30) Foreign Application Priority Data
Dec. 21, 2010 (EP) .................................... 10196224

(51) Int. Cl.
*A61M 5/00* (2006.01)
*A61M 5/24* (2006.01)
A61M 5/28 (2006.01)

(52) U.S. Cl.
CPC ......... *A61M 5/2459* (2013.01); *Y10T 29/49826* (2015.01); *A61M 2005/2477* (2013.01); *A61M 5/28* (2013.01); *A61M 5/24* (2013.01); *A61M 5/2455* (2013.01); *A61M 5/2466* (2013.01)

(58) Field of Classification Search
CPC ... A61M 5/24; A61M 5/2455; A61M 5/2459; A61M 5/2466; A61M 5/28; A61M 5/286; A61M 2005/2403; A61M 2005/2407; A61M 2005/2433; A61M 2005/2437; A61M 2005/244; A61M 2005/2477; A61J 1/16
USPC .......................... 604/201, 240–244, 411–414
See application file for complete search history.

(56) References Cited

U.S. PATENT DOCUMENTS 3,491,757 A * 1/1970 Arce .............................. 604/242
6,126,646 A * 10/2000 Hansen et al. ................. 604/256

(Continued)

FOREIGN PATENT DOCUMENTS

| GB | 2467904 | 8/2010 |
|---|---|---|
| WO | 2008/048750 | 4/2008 |
| WO | 2011/045386 | 4/2011 |

OTHER PUBLICATIONS

International Search Report for Int. App. No. PCT/EP2011/073379, completed Jan. 17, 2012.

*Primary Examiner* — Andrew Gilbert
(74) *Attorney, Agent, or Firm* — McDonnell Boehnen Hulbert & Berghoff LLP

(57) ABSTRACT

The present invention relates to a cartridge holder assembly for a drug delivery device comprising of a cartridge holder adapted to receive a cartridge filled with a medicament to be dispensed by the drug delivery device, wherein the cartridge holder comprises a first through opening at a distal end section to receive a piercing element adapted to penetrate a sealing member of the cartridge, a support structure adjacently arranged to the first through opening; and a constriction member arranged between the support structure and a distal end face of the cartridge and having a second through opening smaller than the first through opening.

9 Claims, 2 Drawing Sheets

(56) References Cited

U.S. PATENT DOCUMENTS

| | | | |
|---|---|---|---|
| 8,574,214 B2* | 11/2013 | Kuhn et al. | 604/415 |
| 2003/0144633 A1* | 7/2003 | Kirchhofer | 604/201 |
| 2007/0078394 A1* | 4/2007 | Gillespie, III | 604/134 |
| 2009/0312715 A1* | 12/2009 | Monson et al. | 604/201 |
| 2011/0301548 A1* | 12/2011 | Young | 604/200 |
| 2013/0030378 A1* | 1/2013 | Jugl et al. | 604/201 |

* cited by examiner

CARTRIDGE HOLDER ASSEMBLY FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2011/073379 filed Dec. 20, 2011, which claims priority to European Patent Application No. 10196224.9 filed Dec. 21, 2010. The entire disclosure contents of these applications are herewith incorporated by reference into the present application.

FIELD OF THE DISCLOSURE

The present invention relates to drug delivery devices and in particular to pen-type injectors, that is to injectors of the kind that provide to administer by injection of medicinal products from a multidose cartridge. In particular, the present invention relates to such injectors, where a user may set and dispense the dose.

BACKGROUND

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where a medicinal product is administered on a regular or irregular basis over a short term or long-term period.

In order to accommodate with these demands, drug delivery devices have to fulfil a number of requirements. First of all, the device must be robust in construction, yet easy to use in terms of handling and in understanding by the user of its operation and the delivery of the required dose or medicament. Further, the dose setting must be easy and unambiguous. Where the device is to be disposable rather than reusable, the device should be inexpensive to manufacture and easy to dispose. Moreover, the device should be suitable for recycling. To meet these requirements, the number of parts required to assemble the device and the number of material types the device is made from need to be kept to a minimum.

The medicinal product to be dispensed by means of the drug delivery device is typically provided in a disposable or replaceable cartridge, such as a vial, ampoule or carpule comprising a piston slidably disposed in the barrel of the cartridge. The piston is to be operably engaged with a piston rod or drive ram of the drug delivery device's drive mechanism. By applying thrust to the cartridge's piston in distal direction—that is towards the patient in the present context—a predefined dose of the liquid drug can be dispensed and expelled from the cartridge.

Cartridges as they are typically used with drug delivery devices, such as pen-type injectors are typically sealed by means of a septum. Such a septum is commonly designed as rubber stopper providing an air-tight seal but being pierceable by piercing elements such as needles or cannulae.

A well-known cartridge holder assembly 10 is illustrated in cross section in FIG. 1. This cartridge holder assembly 10 for a drug delivery device comprises a cartridge holder 14 adapted to receive a cartridge 12, which is hermetically sealed with a flexible and deformable septum 22. At its lower and distal end section, the cartridge holder 14 is threadedly engaged with a needle mount 16. Said mount or needle holder 16 comprises a threaded cylindrical portion allowing to screw the needle holder 16 on the threaded neck portion of the cartridge holder 14. At its lower and distal end section, the mount 16 comprises a flange-like bottom face 17, which in a concentrically inner section holds the injection needle or cannula 20.

During an assembly procedure of the needle holder 16, its proximally located needle 20 penetrates the septum 22 with a tipped end. In this way, a fluid-transferring connection for the purpose of dose dispensing can be established. Additionally, the distal and free end of the needle 20 can be provided with a replaceable needle cap 19. Also, the entire cartridge holder assembly 10 can be covered and protected by a protective cap 18.

Depending on manufacturing tolerances and the mutually corresponding design of cartridge 12 and cartridge holder 14, an axial gap 24 of variable size is typically formed between the bottom portion 17 of the needle holder 16 and the distal end face of the cartridge 16. Axial size of this free space area 24 may vary, e.g. due to manufacturing and assembly tolerances. In particular, during dispensing of a dose of the medicinal fluid contained in the cartridge 12, a respective fluid pressure is built-up, which, due to the inherent elasticity of the septum 22, leads to a respective axial expansion of the septum 22. As a consequence, the septum 22 may almost entirely fill said free space area 24 during a dispensing procedure.

Due to its elastic properties the septum 22 will store elastic energy during dose dispensing. But as soon as the fluid pressure returns to an initial value after a dose dispensing procedure, the septum 22 relaxes into its initial configuration, which is accompanied by a retraction of the expanded section of the septum 22 back into the cartridge 12. However, also such a retracting motion may in turn lead to a built-up of a non-negligible fluid pressure enhancement and, as a consequence, a certain amount of medicinal fluid may be supplementally expelled from the cartridge 12, which can be typically observed in the form of post-dispending droplet formation at the distal tip of the needle 20.

It is therefore an object of the present invention, to provide an improved cartridge holder assembly for a drug delivery device, which counteracts generation of droplets after termination of a dose dispensing procedure. It is a further object, to provide an effective means adapted to prevent septum deformation during dose dispensing. Furthermore, the invention focuses on an inexpensive as well as on a stable and robust design of a drug delivery device.

SUMMARY

The present invention provides a cartridge holder assembly for a drug delivery device which is adapted to dispense a dose of a medicament or medicinal product provided in a cartridge. The cartridge holder assembly comprises a cartridge holder, which is adapted to receive a cartridge, typically designed as vial, carpule or ampoule. Said cartridge is readily filled or is to be filled with a liquid medicament to be dispensed by the drug delivery device in a well-defined way, typically by way of injection.

The cartridge, to be positioned in the cartridge holder is hermetically sealed in distal direction by means of a flexible and deformable sealing member, such like a septum, which is penetrable by a piercing element, e.g. by an injection needle or a cannula. The piercing element is to be releasably mounted on the cartridge holder by way of a needle assembly to become threadedly engaged with is distal portion with the cartridge holder. For this purpose, the cartridge holder comprises a first through opening at its distal end section to receive the piercing element. The piercing element is adapted to penetrate the sealing member of the cartridge in order to establish a fluid-transferring coupling to the inside volume of the cartridge.

Additionally, the cartridge holder assembly, in particular the cartridge holder itself comprises a support structure which is adjacently arranged to the first through opening. The cartridge holder assembly further comprises a constriction member arranged between the support structure of the cartridge holder and a distal end face of the cartridge. Said constriction member comprises a second through opening which is smaller in diameter than the first through opening of the cartridge holder. This way, the constriction member effectively reduces the diameter of a distally located through opening of the cartridge holder assembly.

The size of the second through opening is designed such that the piercing element may still penetrate the sealing member disposed inside the cartridge holder. However, by reducing the diameter of the second through opening, elastic deformation of the cartridge's sealing member can be effectively counteracted. The constriction member serves as a stabilizing structure and reduces elastic deformation of the septum. Hence, the volume and size of a septum extension area between a needle holder and a cartridge holder assembly can be advantageously reduced.

Unintentional expansion of the septum during dose dispending conditions can be at least reduced or can be entirely inhibited. Due to the structural stabilization of the sealing member or septum of the cartridge, magnitude and impact of an elastic relaxation process of the septum after termination of a dose dispensing procedure can be advantageously reduced, thus providing a respective reduction of droplet generation.

According to a preferred embodiment, the constriction member is of circular or disc-like shape. Preferably, the overall geometry of the constriction member is adapted to the geometry and dimensions of the cartridge holder and its support structure. Typically, the cartridge holder is of substantially cylindrical shape and comprises a respective circular symmetric support structure adapted to receive a correspondingly shaped disc-like constriction member of circular shape.

In another preferred embodiment, the constriction member is designed as an insert piece to be arranged or positioned between the distal end face of the cartridge and a proximal support face of the support structure.

When the constriction member is designed as a separate piece the size of the second through opening provided in the constriction member as well as the overall geometry of said constriction member may be modified and adapted to a variety of different piercing assemblies or piercing elements. Hence, the diameter of the second through opening arranged in the constriction member may correspond to the diameter of the piercing element to be arranged therethrough. Depending on the type of cartridge to be used, an appropriately dimensioned constriction member with a through opening of variable diameter can be inserted into the cartridge holder.

In a further preferred embodiment, first and second through openings are concentrically arranged with respect to each other. Moreover, first and/or second through openings may feature similar and/or identical geometry. First and second through openings are preferably of circular geometry.

In still another embodiment, the constriction member comprises a sheet metal disc. Hence, the constriction member is made of sheet metal and therefore provides a comparatively rigid and structurally stiffened structure, which is able to withstand a distally directed pressure effect arising or emanating from the elastically deformable septum during dose dispensing. A sheet metal disc is also very simple and non-expensive to manufacture and may even allow to equip or to retrofit existing cartridge holders with a constriction member.

In a further preferred embodiment the sheet metal disc comprises a thickness of less than 1 mm, less than 0.5 mm, less than 0.2 mm, or even less than 0.1 mm or 0.05 mm. Depending on the material of choice for the sheet metal disc, even a very thin disc featuring a thickness in the sub-millimeter range may already provide sufficient structural support for effectively counteracting septum deformation during dose dispensing.

By making use of e.g. an aluminum or steel disc, a thickness in the range of sub-millimeters for the sheet metal disc can be attained which allows to leave the general design and geometry of the cartridge holder almost unaffected. Hence, by making use of a rather thin stabilizing disc as the support structure, existing cartridge holders may simply be retrofitted with said constriction member and do not require any further modification.

In another aspect, the support structure comprises a radially inwardly directed flange portion integrally formed with the cartridge holder. The radially inwardly directed flange portion may even form a distal end face of the cartridge holder. Said flange portion may abut in distal direction with a bottom face of a needle assembly and said flange portion may further abut with the constriction member in proximal direction. Therefore, the radially inwardly directed flange portion may provide a distal abutment for the disc-shaped constriction member to be squeezed between the support structure and the cartridge to be mounted in the cartridge holder.

It is of further benefit, when the flange portion circumferentially surrounds the first through opening. Having a circumferential flange portion at the distal end of the cartridge holder, axially, in particular distally directed mechanical forces can be homogeneously absorbed. Alternatively, the flange portion may comprise numerous radially extending slits, allowing for an at least slight axial deformation of the flange portion if it becomes subject to respective axially directed mechanical pressure.

In a further preferred embodiment, the radially inwardly protruding support structure comprises at least one proximal abutment surface to receive the constriction member. Here, it is even conceivable, that abutment face and constriction member comprise mutually corresponding interlock means, e.g. in form of mutually corresponding form-fitting elements. This way, unintentional disassembly of constriction member and support structure can be effectively prevented in case that the cartridge is removed from the cartridge holder.

In a further advantageous aspect, the constriction member is elastically deformable in axial direction when squeezed between the support structure and the distal end face of the cartridge. For enhancing elastic deformation of the constriction member, it may comprise one or several, e.g. radially extending slits in order to facilitate, to control and/or to modify its generic elasticity. By squeezing the constriction member, axial pressure between cartridge holder and cartridge may built-up and may be maintained when the cartridge is assembled inside the cartridge holder in its final assembly configuration. Since the constriction member may become subject to an elastic or even plastic deformation during assembly of cartridge holder and cartridge, axial tolerances of the cartridge holder and the entire drug delivery device can be at least reduced or even entirely eliminated.

Furthermore, and according to another preferred embodiment, the radially inwardly extending abutment face of the support structure is inclined in distal direction, hence towards the free end of the cartridge holder. This way, the inclination of the abutment face of the support structure may define a respectively inclined elastic deformation of the constriction member when a final assembly configuration of cartridge holder, constriction member and cartridge has been reached. The inclination of the inwardly extending flange of the support structure may define a maximum degree of elastic deformation of the sheet metal disc.

This way and according to a further preferred embodiment, the constriction member is prestressed or elastically deformed and/or comprises a shape that corresponds with the geometry of the support structure, at least when in final assembly configuration.

According to another independent aspect, the invention also provides a drug delivery device for dispensing of a dose of a medicament. Said drug delivery device comprises a cartridge filled with or to be filled with the medicinal product to be dispensed. The drug delivery device further comprises a drive mechanism, which is operably engaged with the cartridge for dispensing of a predefined dose of the medicament. Further, the drug delivery device is characterized by a cartridge holder assembly as described above.

In another but further independent aspect, the invention also provides a method of assembly of a drug delivery device that comprises a cartridge, a drive mechanism and a cartridge holder assembly as described above. The method is characterized by an assembly procedure for assembling cartridge holder and cartridge of a drug delivery device, in particular a pen-type injector. Here, a constriction member is positioned at a distally located support structure of a cartridge holder prior to an assembly of cartridge holder and cartridge. The constriction member serves to reduce the free diameter of a first and distal through opening of the cartridge holder in order to provide a structural stabilization means for the sealing member of the cartridge and to counteract distally directed expansion of the cartridge's sealing septum during dose dispensing.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-desAsp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Trp(O2)25] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in greater detail by making reference to the drawings in which.

DETAILED DESCRIPTION

Figure 1:
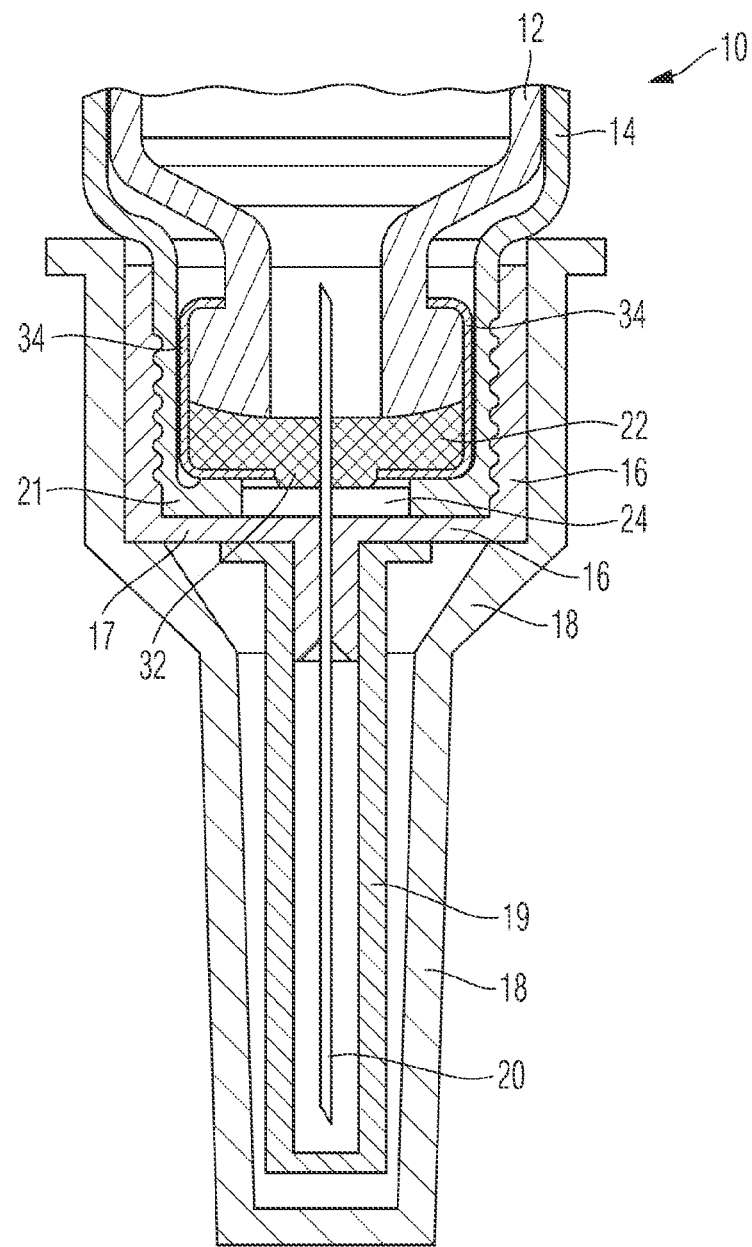
FIG. 1 schematically illustrates a cartridge holder assembly in cross-sectional view according to the prior art.
Figure 2:
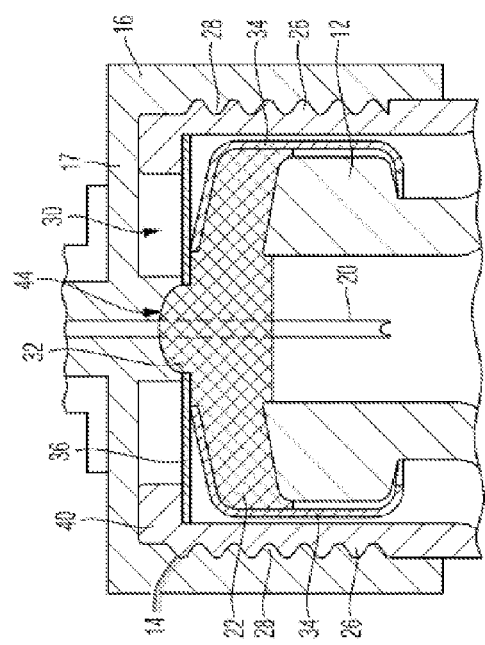
FIG. 2 illustrates a cross-sectional sketch of a cartridge holder assembly according to first embodiment.
Figure 3:
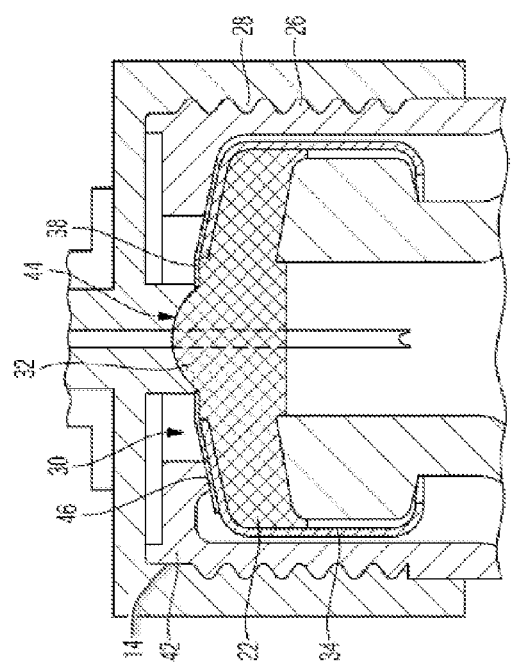
FIG. 3 illustrates a comparable cross-sectional view of the cartridge holder assembly according to a second embodiment.

FIGS. 2 and 3 schematically illustrate a distal end section of a cartridge 12 positioned inside a respective distal end portion of a cartridge holder 14. The cartridge holder 14 is illustrated in FIGS. 2 and 3 with a stepped-down neck portion adapted to receive a respective distal neck portion of a cartridge 12. The illustrated distal end of the cartridge 12 comprises a sealing element, e.g. a penetrable or pierceable septum 22 which is kept in position on top of the body of the cartridge 12 by way of an aluminum cap 34 embracing the distally located head section of the cartridge 12 and the septum 22. The cartridge holder 14, preferably manufactured as an injection moulded thermoplastic component comprises a radially inwardly protruding and circumferential flange portion 40 at its distal end. As illustrated in FIG. 2, said flange portion 40 serves as a support structure for a disc-shaped constriction member 36 preferably comprising a sheet metal disc.

The illustrated distal end section of the cartridge holder 14 comprises an outer thread 26 that corresponds with an inner thread 28 of a needle assembly 16, which is to be screwed onto the cartridge holder 14 until the needle assembly 16 abuts with a distally located flange portion 40 of the cartridge holder with its bottom section 17.

The constriction member 36 serves as a bearing or abutment for the distal end face of the cartridge 12. As can be seen in FIGS. 2 and 3, the metal disc 36, 46 comprises a concentric through opening 44 which is smaller than the free diameter between oppositely located flange portions 40, 42. The through opening 30 of the cartridge holder 14 can be reduced in diameter by means of the constriction members 36, 38.

In this way, an elastic and distally directed deformation or bulged portion 32 of the septum 22 during a dose dispensing action can be at least reduced in size. Consequently, a respective post-dispensing relaxation effect can be reduced and a resulting droplet generation to be observed at a distal but illustrated tip of the needle 20 can be effectively reduced or even anihilated.

As further illustrated in the alternative embodiment according to FIG. 3, the radially inwardly protruding support structure 42 comprises an inclined support or abutment surface 46 facing in proximal direction. By way of such an inclined abutment surface 46, axial and elastic deformation of the constriction member 38 can be limited. In any of the illustrated embodiments according to FIGS. 2 and 3, the constriction member 36, 38 may become subject to mechanical and axially directed pressure or stress and may therefore provide or establish permanent mechanical stress or tension between the cartridge 12 and the cartridge holder 14, thus effectively eliminating inevitable axial tolerances.

The constriction member 36, 38 may be provided as a separate insert piece and may therefore allow to retrofit also existing cartridge holder assemblies featuring a radially inwardly protruding flange portion 40, 42. Since the metal disc may feature a thickness in the sub-millimeter range, preferably between 0.1 mm and 0.2 mm or even below 0.2 mm, less than 0.15 mm, less than 0.1 mm, or less than 0.05 mm, the overall design and geometry of an existing cartridge holder 14 may remain almost unaffected.

Moreover, depending on the type of needle 20 to be penetrated or inserted through the septum 22 of the cartridge 12, transverse size of the diameter of the constriction member's 36, 38 central through opening 44 may vary.

The invention claimed is:

1. A cartridge holder assembly for a drug delivery device comprising:
    a cartridge holder adapted to receive a cartridge filled with a medicament to be dispensed by the drug delivery device, wherein the cartridge holder comprises a first through opening at a distal end section to receive a piercing element adapted to penetrate a sealing member of the cartridge,
    a support structure characterized by
    an intermediary constriction member of circular or disc-like shape arranged between the support structure and a distal most end face of the cartridge and having a second through opening smaller than the first through opening, wherein the constriction member is configured to be received and positioned within the support structure prior to an assembly of the cartridge within the cartridge holder; and
    wherein the support structure comprises a radially inwardly directed flange portion integrally formed with the cartridge holder, wherein the radially inwardly directed flange portion is adjacently arranged to the first through opening, wherein the radially inwardly directed flange portion comprises a proximal abutment surface to receive the constriction member.

2. The cartridge holder assembly according to claim 1, wherein the second through opening is concentrically arranged with the first through opening.

3. The cartridge holder assembly according to claim 1, wherein the constriction member comprises a sheet metal disc.

4. The cartridge holder assembly according to claim 3, wherein the sheet metal disc comprises a thickness of less than 0.2 mm.

5. The cartridge holder assembly according to claim 4, wherein the flange portion circumferentially surrounds the first through opening.

6. The cartridge holder assembly according to claim 1, wherein the constriction member is elastically deformable in an axial direction when squeezed between the support structure and the distal end face of the cartridge.

7. The cartridge holder assembly according to claim 5, wherein the proximal abutment surface is inclined in a distal direction.

8. The cartridge holder assembly according to claim 7, wherein the constriction member is prestressed and/or comprises a shape that corresponds with the geometry of the support structure.

9. A method of assembly of a drug delivery device comprising a cartridge, a drive mechanism and a cartridge holder assembly according to claim 1, wherein the constriction member is positioned within the support structure of the cartridge holder prior to an assembly of the cartridge holder and the cartridge.

* * * * *